United States Patent [19]

Krouthén

[11] 4,447,394
[45] May 8, 1984

[54] METHOD FOR STERILIZATION WITH FORMALIN

[75] Inventor: Jan K. Krouthén, Halmstad, Sweden

[73] Assignee: Aktiebolaget Electrolux, Stockholm, Sweden

[21] Appl. No.: 518,761

[22] Filed: Aug. 1, 1983

Related U.S. Application Data

[60] Continuation-in-part of Ser. No. 182,214, Aug. 28, 1980, abandoned, which is a division of Ser. No. 951,526, Oct. 16, 1978, abandoned.

[30] Foreign Application Priority Data

Oct. 17, 1977 [SE] Sweden .............................. 77116606

[51] Int. Cl.$^3$ ........................... A61L 2/20; A61L 2/06
[52] U.S. Cl. ....................................... 422/27; 422/33; 422/36; 422/114; 422/116; 422/298
[58] Field of Search ....................... 422/27, 33, 36, 26, 422/298, 116, 114, 305

[56] References Cited

U.S. PATENT DOCUMENTS

| | | | |
|---|---|---|---|
| 781,818 | 2/1905 | Fournier | 422/305 X |
| 903,853 | 11/1908 | Garther | 422/27 |
| 1,593,121 | 7/1926 | Gray | 422/26 |
| 2,080,179 | 5/1937 | Merriam et al. | 422/27 |
| 2,125,375 | 8/1938 | Hinegardner | 422/27 X |
| 3,409,389 | 11/1968 | Bjork | 422/26 |
| 3,436,170 | 4/1969 | Lodge | 422/26 |
| 3,598,516 | 8/1971 | Shull et al. | 422/27 |

FOREIGN PATENT DOCUMENTS

| | | | |
|---|---|---|---|
| 763147 | 7/1967 | Canada | 422/26 |
| 2016698 | 10/1970 | Fed. Rep. of Germany | 422/27 |

OTHER PUBLICATIONS

Pickenll, J. K., "Practical System for Steam-Formaldehyde Sterilizing", Laboratory Practice; vol. 24, No. 6; 6/75; pp. 401–404.

Primary Examiner—Barry S. Richman
Attorney, Agent, or Firm—Alfred E. Miller

[57] ABSTRACT

An apparatus and method for sterilizing particles in an autoclave with an atmosphere of formaldehyde and water vapor so that the sterilized articles have tolerable quantities of residue of formaldehyde and paraformaldehyde thereon. In the process, formalin is used which is transformed to a gaseous condition and supplied to the autoclave. The apparatus is provided with a vaporizer for formalin in which the vaporizer is provided with a liquid trap so that the formalin becomes said water vapor and formaldehyde.

5 Claims, 3 Drawing Figures

METHOD FOR STERILIZATION WITH FORMALIN

The present invention is a continuation-in-part of Ser. No. 182,214 filed Aug. 28, 1980, now abandoned, which is a divisional application of parent application Ser. No. 951,526 filed Oct. 16, 1978, now abandoned.

BACKGROUND OF THE INVENTION

Formaldehyde is an easily reacting gas which is toxic and which can cause allergic reactions to people coming into contact with articles containing such gas. It is well known that formaldehyde can be used as a disinfectant for different fields of use. Furthermore, formaldehyde is gaseous at room temperature, but is easily soluble in water, therefore in practice formalin is used which is a solution of about 40% formaldehyde in water. Rather recently, methods have been devised in which sterilization with formaldehyde was made possible. Sterilization in autoclaves with the use of steam is an old, well known method, but articles treated in the autoclave with steam are subject to temperatures of about 110° to 140° C. It has been observed that many articles to be sterilized do not tolerate treatment at so high a temperature and thus other methods and means for sterilization have been sought. Thus, autoclaves using formalin have been suggested. Theoretically, in an autoclave using formalin, sterile articles can be obtained by treatment to about 80° C. However, in practice it has been noted that although sterile items are obtained, at the same time formaldehyde residues and a layer of paraformaldehyde will settle on the articles. The quantity of such residues on the sterilized items varies in accordance with different treatments. Consequently, the use of formalin results in the aforementioned drawback, and also this is an indication that this method is not ideal.

As mentioned hereinbefore, the solution of 40% formaldehyde in water can be used, however it is an object of this invention to improve this known method by which 16 ml. of such solution is used per hundred l. of autoclave volume. The foregoing method has yielded good results and sterilization has been obtained within a temperature range of 60°–80° C., but surprisingly the articles have not been free of residues.

The above disadvantage can be avoided by utilizing the present invention in which in each sterilization process a given small quantity of formalin is supplied to a vaporizer which has a liquid trap and in which the formalin is transformed into water vapor and formaldehyde which is supplied to the autoclave chamber by way of a vapor conduit.

Thus, the present method relates to a process for transforming formalin into formaldehyde and steam prior to the introduction into the autoclave chamber so that no residues of paraformaldehyde remain in the vaporizer or in the conduit connecting the vaporizer with the autoclave chamber.

In order that the invention will be more clearly understood, it will now be disclosed in greater detail with reference to the accompanying drawings, in which.

DESCRIPTION OF THE PREFERRED EMBODIMENT

Figure 1:
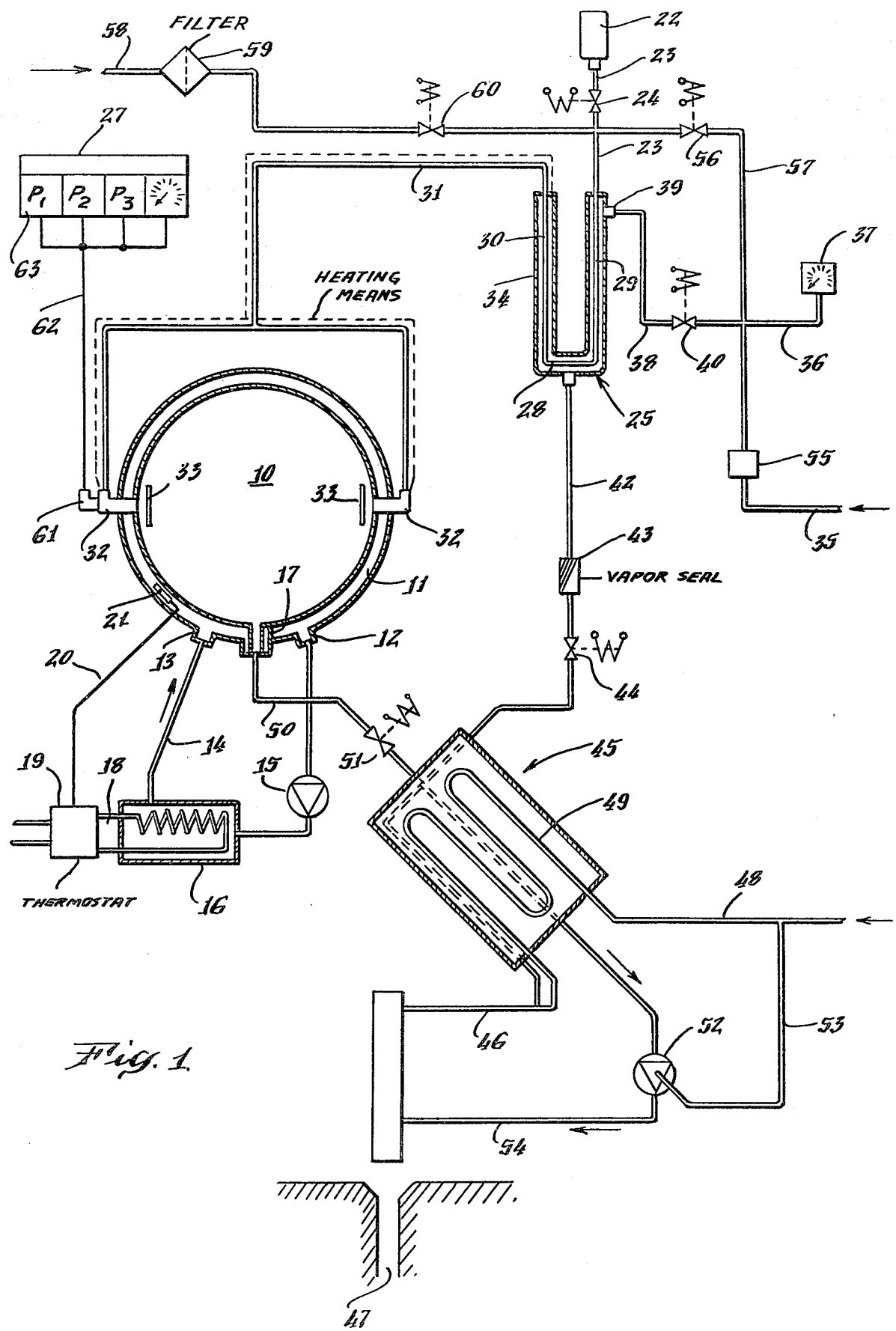
FIG. 1 is a diagrammatic showing of an autoclave operating with formalin and vapor in accordance with the teachings of the present invention.

FIG. 1 shows an autoclave having a chamber 10 with a door (not shown). The chamber 10 is surrounded by a jacket 11 which, in its lower part, has two connections 12 and 13 for a conduit 14 having a circulation pump 15 and a water heater 16. Between the connections 12 and 13 in its lower part the jacket has an intermediate wall 17. A heat transferring medium, such as water, circulates in the jacket 11 and through the circulation conduit 14. An electric heater 18 heats jacket 11 and conduit 14 to a temperature controlled by a thermostat 19 having a wire 20 to a sensor 21 located in the jacket 11.

Treatment medium is supplied to the autoclave chamber 10, for example, from an inverted bottle 22 which contains a proportioned quantity of formalin for a sterilization treatment. A conduit 23, with a magnetic valve 24, extends from the bottle 22 to a vaporizer 25. The bottle 22 has a rubber seal and the conduit 23 a syringe needle. The valve 24 is controlled by a program device 27.

The vaporizer 25 comprises a U-shaped pipe 28 in which one leg 29 is connected to the formalin conduit 23 and the other leg 30 is connected to a supply conduit 31 having two inlets 32 to the autoclave chamber. Inside of each inlet is a shield 33 which spreads the treatment medium that is supplied into the autoclave. The U-shaped pipe 28, 29, 30 has a heating means, which in the embodiment shown, is a jacket 34 heated by steam. A conduit 38 extends from a steam supply conduit 35, having a branch conduit 36 with a manometer 37, to an inlet 39 at the upper part of the steam-heated jacket 34. The conduit 38 has a magnetic valve 40 controlled by the program device 27. Along its entire length the supply conduit 31 has heating means, which are indicated by the dashed line 41, and can be in the form of an electric heater or a vapor conduit.

A condensate drain 42 is led from the bottom of the steam-heated jacket 34 and passes through a vapor seal 43 as well as a magnetic valve 44 controlled by the program device 27. The drain 42 then passes through a condenser 45 to a conduit 46 discharging the accumulated condensate into a drain 47.

The condenser 45 is cooled by water from a water conduit 48 which passes therethrough and also through the condenser in the form of a coil 49. Thereafter, the water is conducted away through the discharge conduit 46. A discharge conduit 50 extending from the bottom of the chamber 10 passes through the condenser 45, and is provided with a magnetic valve 51 connected to the program device 27. After having passed the condenser 45, the discharge conduit 50 passes through a vacuum pump 52, which like the condenser 45, receives water from the conduit 48 by means of a branch conduit 53. The vacuum pump 52 communicates with the drain 47 by way of a discharge conduit 54.

The steam supply conduit 35 is provided with a liquid water separator 55, which can be a cyclone filter, so that the conduit contains dehydrated vapor which is furnished to the formalin conduit 23 ahead of the vaporizer 25 by way of a conduit 57 having a magnetic valve 56. Thus, the vapor supplied to the chamber is conducted through the vaporizer 25 and the heated conduit 31.

After the articles have been treated in the chamber 10 sterile air is drawn through the latter. This air is taken in by means of a supply conduit 58 for atmospheric air, which conduit includes a sterile filter 59 and a magnetic valve 60, and is connected to the formalin conduit 23, so that the air supplied to the chamber, in the same way as when vapor is supplied, is conducted through the vaporizer 25 and the heated conduit 31 to the inlets 32 to the chamber 10.

At the left side of the chamber adjacent the inlet 32 is a connection 61 for a sensor (not shown) connected by wires 62 to indicating and recording instruments 63, which indicate pressure, temperature, and other characteristics of the chamber atmosphere, and which can also be connected to the program device 27.

Referring again to FIG. 1, the chamber is shown with the jacket 11 in section. The chamber may have an end wall and a door, which like the chamber wall, has a jacket heated by water. However, the door can be heated electrically instead. In addition, all connections to the chamber have heating means, so that they can be maintained at a higher temperature than that of the chamber atmosphere, which can be effected by hot water, vapor or by electrical means.

Figure 2:
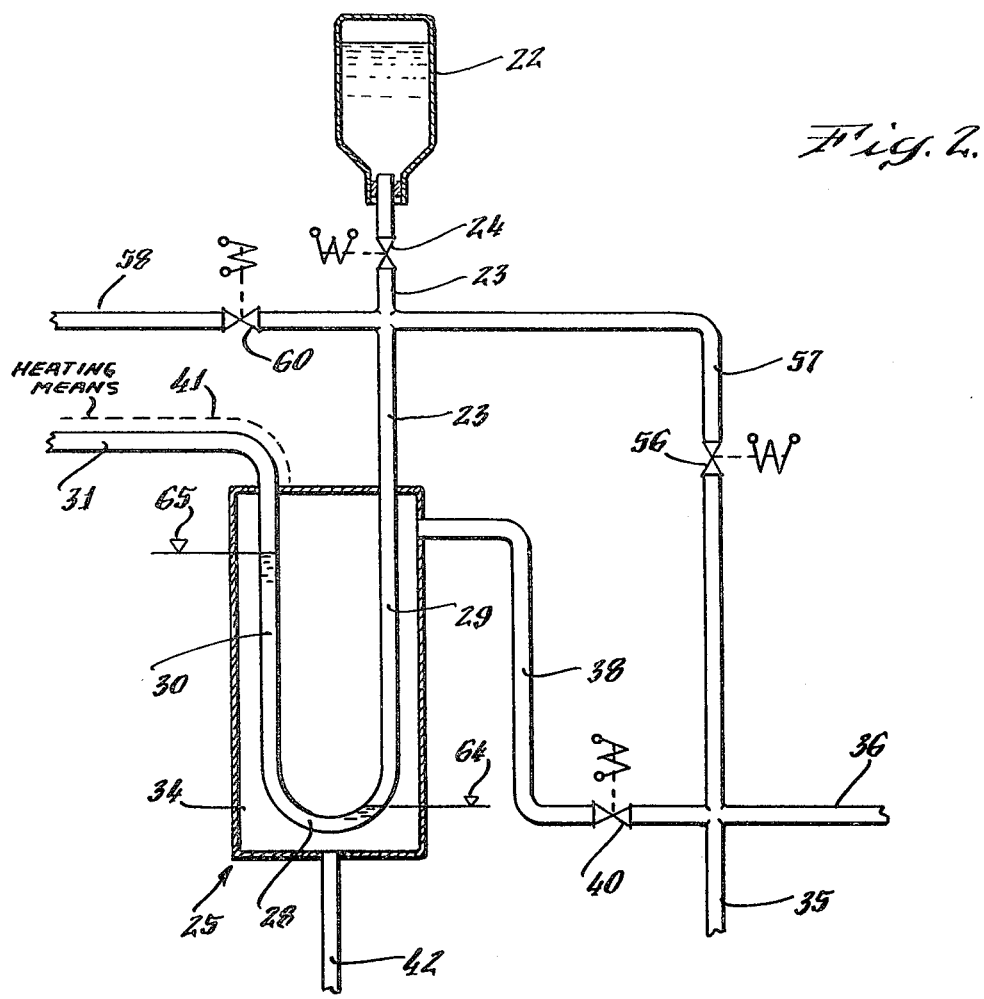
FIG. 2 is a detail of the apparatus in FIG. 1, shown on an enlarged scale.

FIG. 2 shows an enlarged scale, the vaporizer 25, with conduits connected adjacent the vaporizer, as well as the bottle 22 for formalin. When the valve 24 in the formalin conduit is opened, a dose of formalin, which has been prepared in advance in the bottle 22, flows down into the leg 29 of the U-shaped pipe 28. The entire quantity of formalin is transferred at the same time to the U-shaped pipe whose volume must be sufficiently great to hold the quantity of formalin supplied. The jacket 34 surrounding the U-shaped pipe has earlier been heated to above vaporization temperature by means of vapor supplied through the conduit 38. In FIG. 1 the vaporizer is shown as a U-shaped conduit for formalin with a jacket of corresponding shape, but in FIG. 2 the U-shaped pipe 28, is disposed in a jacket 34 which encloses both legs of the pipe. Heating of the formalin causes vaporization, so that water vapor and gaseous formaldehyde are produced. The vapor formed in the left leg 30 leaves the liquid and is conducted through the conduit 31 to the chamber 10, whereas the vapor formed in the right leg 29 fills the vapor space above the leg in the conduit 23 and the connecting conduits 57, 58 to the adjacent valves 24, 56, and 60. Thus, it is important that the above-mentioned vapor space is as small as possible. In this space, a vapor pressure is produced which forces the formalin downwards in the right leg 29 to a level 64 at the bottom of the U-shaped pipe, where the vapor can penetrate the liquid, and rises through the left leg 30 to ultimately be discharged by the conduit to the chamber 10. Thus, the liquid in the left leg is forced upwardly to a level 65. This indicates that the size of the U-shaped pipe has to be dimensioned so that also when liquid is being depressed in the right leg no liquid will be capable of rising in the conduit 31 and flow to the chamber 10. In this manner the vaporizer forms a liquid trap, preventing everything, but clean water vapor and formaldehyde in the form of gas, to be transferred to the chamber.

After vaporization and transfer to the chamber of the formaldehyde, vapor is then supplied to the chamber. The vapor is conducted through the conduit 57 and the U-shaped pipes 29, 30 before being supplied by way of the conduit 31 to the chamber 10. In this manner, additional heat is supplied to the vaporizer and possible residues of formalin in the U-shaped pipe are caused to vaporize, and are carried by the vapor to the chamber.

The mode of operation for sterilization of articles with formalin in accordance with the teachings of the present invention is as follows.

Figure 3:
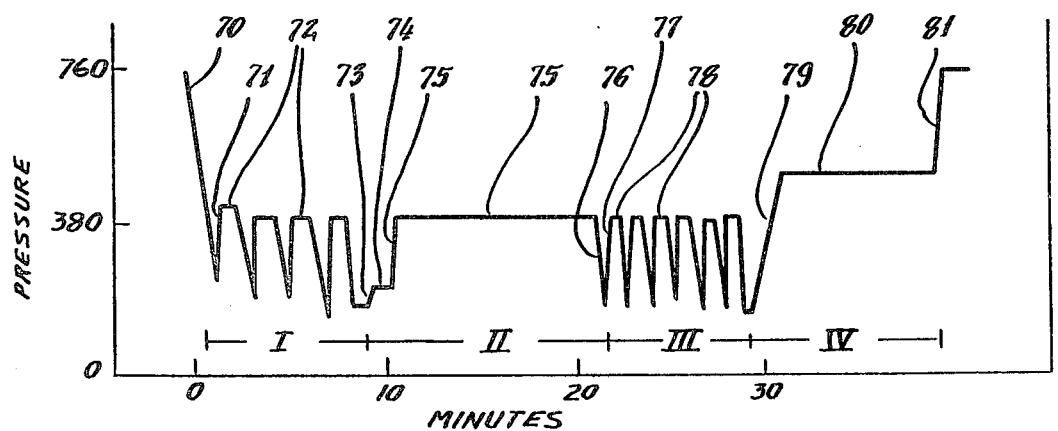
FIG. 3 is a graph of the pressure in the autoclave plotted against time.

The articles are placed in the chamber 10 and the door is closed. At this stage, the chamber contains articles and atmospheric air of about the same temperature and pressure as the ambient. This stage of the process corresponds to the time 0 of FIG. 3, which shows the variation of the pressure in the autoclave chamber depending on the time during a sterilization treatment. The jacket 11 of the chamber 10 is heated, in case it is not already warm, by operating the circulation pump 15 and the heater 16. When the sterilization temperature has been reached, the vacuum pump 52 is started and the pressure in the chamber is reduced, as shown by the line 70 in the diagram. When the intended negative pressure has been reached, vapor is admitted into the chamber according to the line 71 so that a temperature of about 80° C. is obtained at about 50% of negative pressure. This condition is maintained during a given time, about 1 minute, as indicated by the line 72. Thereafter, vacuum suction and vapor supply during given periods are repeated several times. These pulsations are of great importance. On one hand, air in the chamber 10 and in the articles is removed, and on the other hand vapor is supplied which to some extent condenses on the articles, and to a certain degree increases the temperature of the articles. The amount of condensed moisture is not very large but it is of great importance because it changes the subsequent treatment with formaldehyde. Quite dry bacteria cannot be killed at the low temperature intended for the treatment, at least not in a short period of time. The moisture dissolves possible salts and crystals formed or blood rests on the articles, and it also gives some moisture to present bacteria. Since the formaldehyde is easily soluble in water, on the subsequent treatment, it will reach the bacteria and act on them.

The pre-pulsation described above has proved to be effective for packing types and spore specimens of present types and also in the most difficult cases, which occur when sterilization is made with a very small charge in the chamber 10. This latter is the most difficult case, because a small amount of articles in the chamber is heated by radiation from the chamber wall to such a high temperature that condensation of the vapor is made difficult.

The periods of supply of vapor in the temperature range of 80° C., or a delay before subsequent negative pressure during the pulsation, results in preheating of the articles at 80° C. so that the vapor will enter and condense as well as increase the temperature of the articles. This produces a better microbiological effect, sterilization, during the treatment. The added quantity of formaldehyde can be smaller than heretofore believed possible by means of the foregoing improved moistening process, which is wholly controlled and can be repeated during each treatment. In spite thereof, a real bacteriological killing effect is obtained. It has proved that the quantity of formalin supplied can be reduced to almost a quarter of the quantity previously used. An interesting consequence of this fact is that the amount of residues of undesired substances on the sterilized articles is much smaller than occurs in known processes. This means that by applying the teachings of the present invention during after-treatment of articles, the residues can be removed to such an extent that the articles ready for practical use can be considered to be free of residues.

After the pre-treatment, and with negative pressure in the chamber 10, formalin is supplied to the U-shaped pipes 29, 30 of the vaporizer and vapor of about 110° C. is supplied to the jacket 34 of the vaporizer through the conduit 38. The formalin is vaporized and vapor, which is free of water, and formaldehyde in the form of gas, which is free of undesired substances, are supplied to the chamber during a short period 73. The vaporizer is emptied of its contents by heating the vaporizer to about 110° C. Thus, only steam and formaldehyde gas leaves the vaporizer when heated. The conduit 31 is heated above the treatment temperature of 80° C. in the autoclave chamber in order to prevent the condensation of steam in conduit 31, and the prevention of formaldehyde gas dissolving in a condensed steam to gradually polymerize into paraformaldehyde, which could clog conduit 31. The pressure rises somewhat. After a short period of time 74, steam 75 is supplied to the system up to the intended treatment pressure, which is about 50% of negative pressure at a temperature of about 80° C. in the chamber 10. This condition is maintained for about 10 minutes, and it is controlled automatically by the program device 27 by some supply of vapor.

It should be noted that the pre-pulsation and supply of formalin discussed above is an important provision for obtaining sterilization of the treated articles on each treatment.

For safety reasons, an after-treatment is utilized after the sterilization period. In accordance with the teachings of the present invention this after-treatment comprises several pulsations, each one meaning that the vacuum pump 52 is operated during a period 76, while cold water is supplied to the condenser 45 by the conduit 48 and the valve 51 is open, so that the chamber atmosphere drawn out through the condenser is condensed and carried to the drain 47 in liquid form. Then steam is again supplied to the chamber during a period 77, and it has been proved to be important that the condition is maintained during a short period 78 after the supply of steam. Thereafter, negative pressure and steam supply during given periods are repeated a number of times. In this way, the steam supplied is each time caused to penetrate the articles in the chamber, and together with formaldehyde to be drawn out during the following negative pressure. This after-treatment is of course facilitated by the fact that the treatment has been carried out with a smaller amount of formalin than earlier methods, per liter of chamber volume. It has proved, however, that this after-treatment results in a better washing than previous known methods and a more reproducible result. However, it has also been shown that both the time of the after-treatment and the number of pulsations are of importance for the result. By an after-treatment during about 10 minutes, and by six pulsations, the most effective purification process is achieved. It has been observed that less or more pulsations give an inferior result.

The present method and apparatus results in only steam and formaldehyde gas discharging from conduit 31 into the autoclave chamber, and no residues of formalin or paraformaldehyde remain in the conduit 31 or in the vaporizer 25.

The above-described method does not only result in low quantities of residues but is interesting also in other respects. It can be noticed that during the sterilization process period 75 the gas phase in the chamber contains a considerably greater percentage of formaldehyde than earlier, and this has a favorable influence, not only on the residues, but also on the sterilization efficiency during the treatment.

After the after-pulsations 76–78 are finished, and with a negative pressure in the autoclave, sterile air is supplied through the conduit 58 and the vaporizer 25 to the chamber 10, so that a pressure is obtained in the chamber which is a little higher than the treatment pressure. Simultaneously, the vacuum pump 52 is kept in operation. The increase of pressure is marked by the period 79 in FIG. 3. The injection of sterile air through the chamber is then permitted to continue with maintained pressure during a period 80, after which the pump 52 is stopped, and air continues to be supplied during a period 81 until the pressure has been equalized, and is atmospheric in the chamber 10. The process is then completed and the door can be opened, and the articles therein removed for direct use, or for storage.

What is claimed is:

1. A method of sterilizing articles in a heated autoclave chamber having an atmosphere of formaldehyde and water vapor while preventing the formation of formalin and/or paraformaldehyde residues in the autoclave chamber and comprising the steps of: supplying a given quantity of formalin through a conduit to a vaporizer having a jacket surrounding it, the vaporizer being formed as a liquid trap for receiving said quantity of formalin and preventing overflow of liquid from said quantity out of the vaporizer, heating said jacket to 110° C. to thereby transform said formalin into water vapor and formaldehyde in said vaporizer, and passing said water vapor and formaldehyde through a vapor conduit to said autoclave chamber, said vapor conduit being maintained at a temperature above the temperature of said chamber atmosphere and exposing articles to be sterilized to said formaldehyde and water vapor at a temperature elevated above room temperature for a period of time sufficient to sterilize said articles, whereupon the formaldehyde-water vapor mixture is removed from said autoclave chamber.

2. The method as claimed in claim 1 wherein said vaporizer is heated by steam.

3. The method as claimed in claim 1 wherein after the sterilization period has been completed, air is conducted through said vaporizer and said vapor conduit to said chamber.

4. The method as claimed in claim 1 wherein steam is conducted through said vaporizer and said vapor conduit and supplied to said chamber following the step of passing the formaldehyde-water vapor mixture into said autoclave chamber for maintaining the chamber atmosphere.

5. The method as claimed in claim 4 wherein prior to said steam being supplied to said chamber, said steam is purged of any liquid water therein.

* * * * *